United States Patent [19]

Gelbein et al.

[11] Patent Number: 4,496,752

[45] Date of Patent: Jan. 29, 1985

[54] PRODUCTION OF EPOXY COMPOUNDS FROM OLEFINIC COMPOUNDS

[75] Inventors: Abraham P. Gelbein, Plainfield; Joon T. Kwon, Freehold Township, Monmouth County, both of N.J.

[73] Assignee: The Lummus Company, Bloomfield, N.J.

[21] Appl. No.: 35,558

[22] Filed: May 3, 1979

[51] Int. Cl.$^3$ ............... C07D 301/26; C25B 1/46; C25B 3/02

[52] U.S. Cl. ............... 549/521; 549/520; 549/522; 204/80

[58] Field of Search ............ 260/348.21, 348.18, 260/348.22; 204/80; 549/520, 521, 522

[56] References Cited

U.S. PATENT DOCUMENTS

| | | | |
|---|---|---|---|
| 2,694,722 | 11/1954 | Katz | 260/453 R X |
| 4,008,133 | 2/1977 | Gelbein et al. | 260/348.18 |
| 4,126,526 | 11/1978 | Kwon et al. | 260/348.21 |

FOREIGN PATENT DOCUMENTS 1291328  3/1969  Fed. Rep. of Germany ............ 260/348.21

*Primary Examiner*—Norma S. Milestone
*Attorney, Agent, or Firm*—Elliot M. Olstein

[57] ABSTRACT

Chlorine and tertiary alkanol dissolved in an inert organic solvent are reacted with aqueous alkali to produce tertiary alkyl hypochlorite which is recovered in the organic solvent and reacted with water and olefinically unsaturated compound to produce chlorohydrin and tertiary alkanol. Chlorohydrin and tertiary alkanol recovered in the organic solvent are contacted with aqueous alkali to produce the epoxy compound, and tertiary alkanol recovered in the organic solvent is recycled to hypochlorite production. The process may be integrated with the electrolytic production of chlorine, with an appropriate treatment of the recycle aqueous stream when required.

18 Claims, 1 Drawing Figure

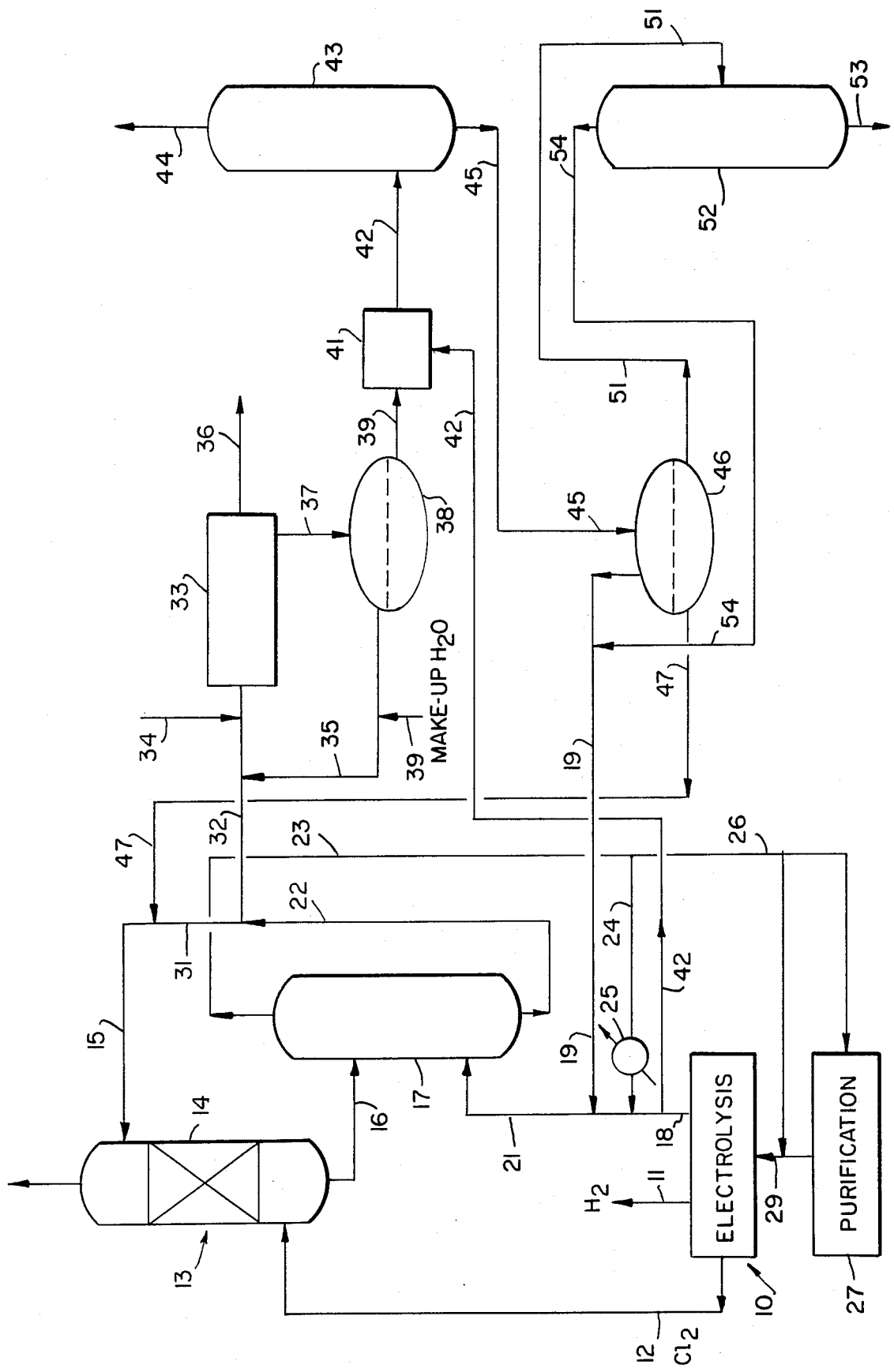

PRODUCTION OF EPOXY COMPOUNDS FROM OLEFINIC COMPOUNDS

This invention relates to the production of epoxy compounds, and more particularly to a new and improved process for producing epoxy compounds from olefinically unsaturated compounds via the chlorohydrin.

U.S. Pat. Nos. 4,008,133 and 4,126,526 describe a process for producing epoxy compounds from olefins, via the chlorohydrin, and is particularly related to a process for producing epoxy compounds which is integrated with an electrolytic process for producing chlorine, whereby the epoxy compound can be produced from olefin and water, as net starting materials. The present invention is directed to an improvement in the type of process described in such patent.

In accordance with the present invention, there is provided an improved process for producing an epoxy compound from an olefinically unsaturated compound employing a hypochlorite for converting olefin to chlorohydrin and subsequent saponification of the chlorohydrin to the epoxy compound wherein hypochlorite production, chlorohydrin production and saponification are effected in the presence of an inert organic solvent to thereby effectively recover the organic components produced in such steps.

More particularly, chlorine and tertiary alkanol dissolved in an inert organic solvent are reacted with aqueous alkali to produce tertiary alkyl hypochlorite. Tertiary alkyl hypochlorite dissolved in the inert organic solvent is recovered and reacted with olefinically unsaturated compound and water to produce the corresponding chlorohydrin and tertiary alkanol. Chlorohydrin and tertiary alkanol in the organic solvent is recovered and saponified with aqueous base to produce the epoxy compound. The epoxy compound is recovered as product, and tertiary alkanol dissolved in the inert organic solvent is recovered and recycled to the hypochlorite production.

The organic solvent employed in the process is inert, immiscible with the aqueous phases present in the process and is a solvent for chlorine as well as hypochlorite, alkanol, and chlorohydrin employed and/or produced in the process. The term "inert" as used herein means that the solvent does not adversely affect the various reactions. As representative examples of such solvents, there may be mentioned: chlorinated hydrocarbons, including chlorinated aromatics; and chlorinated aliphatics (saturated) e.g., O-dichlorobenzene, chlorinated paraffins, such as carbon tetrachloride, chloroform, dichloropropane, etc.; ketones; e.g., methyl ethyl ketone, methyl isobutyl ketone, acetone, and the like. Such solvents may be employed alone or as a mixture of two or more thereof. In accordance with a preferred aspect, the organic solvent or its azeotrope with water has a boiling point less than the aqueous caustic solution employed for the saponification to facilitate recovery of the epoxy compound by steam stripping; i.e., reduction of reboiler temperature and lower steam consumption.

The aqueous alkali employed for the hypochlorite production and saponification may be the same or different alkali. Similarly, the alkali can be obtained from any one of a wide variety of sources. In accordance with a preferred procedure, the epoxy production is integrated with an electrolytic process for producing chlorine; however, the scope of the invention is not limited to such a preferred procedure. For example, chlorine can be obtained from other sources and/or alkali can be provided other than from the electrolytic cell.

In accordance with the preferred aspect of the present invention, gaseous chlorine is produced in an electrolytic cell by the electrolysis of an aqueous brine solution, with chlorine being produced at the anode and hydrogen at the cathode. Gaseous chlorine produced in the electrolysis cell and tertiary alkanol, dissolved in an inert organic solvent, is reacted with an aqueous solution, containing sodium hydroxide and sodium chloride, obtained from the cathode compartment of the electrolytic cell to produce a tertiary alkyl hypochlorite. The thus produced tertiary hypochlorite, dissolved in the inert organic solvent is then reacted with an olefinically unsaturated compound and water to produce the corresponding chlorohydrin and tertiary alkanol. Chlorohydrin and tertiary alkanol dissolved in the inert organic solvent is contacted with an aqueous solution of sodium hydroxide and sodium chloride, obtained from the cathode compartment of the electrolytic cell, to effect saponification of the chlorohydrin to the corresponding epoxy compound, which is recovered as reaction product.

Aqueous solution, which is recovered from the hypochlorite production and saponification reactions, containing sodium chloride, purified, if needed, to remove dissolved organics, as advantageously described in U.S. Pat. No. 4,126,526, is recycled to the electrolytic cell. Tertiary alkanol dissolved in the organic solvent is recovered from the saponification reaction, and recycled to the hypochlorite production.

The electrolysis cell used for producing chlorine from an aqueous brine may be any one of the wide variety of electrolytic cells known in the art, and is preferably of the diaphragm type. The use of such a cell is deemed to be well within the scope of those skilled in the art and, accordingly, no further explanation in this respect is deemed necessary for complete understanding of the present invention.

In general, in the integrated process, the electrolytic feed to the anode has a sodium chloride concentration from about 170 to about 400 grams per liter of water, and preferably from about 280 to about 400 grams per liter of water. In the electrolytic cell, chlorine is produced at the anode and hydrogen and sodium hydroxide are produced at the cathode.

Chlorine produced in the electrolytic cell is then dissolved in the inert organic solvent. Such inert organic solvent is conveniently a recycled solvent recovered from the saponification step which also contains the tertiary alkanol produced in the chlorohydrin production step. The tertiary alkanol is preferably a tertiary alkanol having from 4 to 6 carbon atoms, and most preferably tertiary butanol or tertiary amylalcohol. The solution of chlorine and tertiary alkanol in the inert organic solvent is then contacted with the caustic cell liquor obtained from the electrolytic cell to produce the hypochlorite. The dissolution of chlorine permits hypochlorite production by liquid-liquid reaction which is an improvement over the gas-liquid reaction previously employed.

In general, the hypochlorite production is effected at a temperature from about 5° F. to about 220° F., and preferably from about 32° F. to about 160° F. In general, the pressure is in the order of from about 5 to about 100 psia, and preferably from about 10 to about 50 psia. As described in U.S. Pat. No. 4,008,133, the chlorine to sodium hydroxide ratio is preferably at least 0.5:1 (most generally 0.5:1 to 1.05:1) and the tertiary alkanol to sodium hydroxide mole ratio is from 0.75:1 to 1.1:1.

Hypochlorite dissolved in the organic solvent is then reacted with an olefinically unsaturated compound and water to produce the corresponding chlorohydrin and tertiary alkanol. The chlorohydrination of the olefinically unsaturated compound is preferably effected at a temperature of from about 32° F. to about 160° F., most preferably at a temperature from about 70° F. to about 140° F., and at a pressure from about 1 psig to 100 psig. It is to be understood, however, that such conditions are only illustrative of preferred conditions, and a selection of particular conditions, as well as a selection of a reactor scheme, is deemed to be within the scope of those skilled in the art.

As disclosed in U.S. Pat. No. 4,008,133, the water employed in the chlorohydrin production should not contain a chloride ion concentration in excess of 1 mole/liter and preferably should not exceed 0.1 mole/liter. Greater amounts could be used, but such greater amounts may minimize chlorohydrin production by the production of more fully chlorinated byproducts.

The use of an organic solvent in the chlorohydrin production offers the further advantage that there is an in situ extraction of chlorohydrin, which minimizes byproduct production; e.g., in the production of propylene chlorohydrin, bis-chloropropyl ether byproduct is produced in the aqueous phase.

In accordance with a preferred procedure, it has been found that the presence of some salt in the aqueous portion favors extraction of the chlorohydrin and t-alkanol product into the organic phase, thereby facilitating subsequent separation of the effluent into an aqueous phase, for recycle to the chlorohydrin production, and an organic phase, which includes the t-alkanol and chlorohydrin as feed to the saponification. Such salts may include one or more of sodium chloride, sodium sulfate, sodium carbonate, potassium carbonate, calcium chloride, potassium fluoride, etc. Sodium sulfate may be preferred. The salt is employed in a concentration which enhances extraction of organics into the organic phase without adversely affecting chlorohydrin production.

Thus, in accordance with the present invention, the chlorohydrin effluent is separated into an aqueous phase, which is recycled to the chlorohydrin production reactor, in a manner consistent with the procedure of U.S. Pat. No. 4,008,133, and an organic phase, containing the organic solvent, chlorohydrin and t-alkanol (with only a minimal amount of dissolved water) which may be employed as feed to the saponification. Such organics are therefore recovered without requiring distillation.

The organic phase recovered from the chlorohydrin production is then contacted with a suitable base to effect saponification of the chlorohydrin to the corresponding epoxy compound. The base can be any suitable hydroxide, such as, for example, an alkali hydroxide or an alkaline earth metal hydroxide. In accordance with the preferred embodiment, saponification is effected with sodium hydroxide, with such sodium hydroxide being provided in the cell liquor obtained from the cathode compartment of the electrolytic cell, which cell liquor contains both sodium hydroxide and sodium chloride.

In general, such saponification is effected at a temperature from about 150° F. to about 250° F., preferably from about 200° F. to about 230° F., at the autogenous pressure of the system. The saponification is basically effected as described in U.S. Pat. No. 4,008,133. As a result of such contact, the chlorohydrin is converted to the corresponding epoxy compound, and sodium hydroxide present in the cell liquor is converted to sodium chloride.

The epoxy compound may be recovered by a stripping operation, with the saponification preferably being conducted as a combination saponification-stripping operation. The presence of organic solvent during the saponification reduces the reboiler temperature and thereby steam requirements. Such reduction minimizes the formation of glycol by-product.

In accordance with the present invention, the t-alkanol is preferentially extracted into the organic phase for recycle to the hypochlorite production. Such preferential extraction is favored by a high salt concentration, in the aqueous phase, and in general, the salt concentration of the aqueous phase recovered from the saponification is sufficient to favor such preferential extraction. In addition, preferential extraction into the organic phase is favored by higher temperatures, i.e., the temperatures at which saponification is effected. The adjustment of salt concentration and/or temperature, if required, to achieve the desired extraction is deemed to be well within the scope of those skilled in the art from the teachings herein. In general, the temperature and salt concentration resulting from the saponification will result in preferential extraction of the tertiary alkanol into the organic phase.

The aqueous brine solution recovered from the saponification is ultimately recycled to the electrolysis cell. Such brine solution may be initially introduced into the hypochlorite production reactor to effect conversion of any t-alkanol to hypochlorite. As a result, complete extraction of the t-alkanol into the organic phase, although preferred, is not required. The recycle brine solution, if need be, could be variously treated, as in U.S. Pat. No. 4,126,526, to remove organics before being charged into the electrolysis cell.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formula:

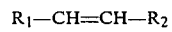

$$R_1-CH=CH-R_2$$

wherein $R_1$ and $R_2$ are each separately either hydrogen; alkyl; halo, naphthyl or phenyl substituted alkyl; halo or alkyl substituted phenyl; phenyl; naphthyl; halo or alkyl substituted naphthyl; alkenyl or halo-substituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexene; stibene; butadiene; chloroprene; allyl chloride, allyl bromide; bromoprene; cyclohexene, and cyclopentene.

The epoxy compounds generally produced in accordance with the invention are represented by the following structural formula:

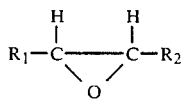

wherein $R_1$ and $R_2$ are as defined above.

The invention will be further described with respect to a preferred embodiment thereof, illustrated in the accompanying drawing wherein:

The drawing is a simplified schematic flow diagram of an embodiment of the process of the present invention.

The preferred embodiment will be particularly described with respect to the production of propylene oxide (1, 2-epoxy propane), but it is to be understood that the embodiment is also applicable to the production of other epoxy compounds.

Referring to the drawing, there is shown an electrolytic cell 10, of a type known in the art, wherein, as known in the art, hydrogen is produced at the cathode, and chlorine at the anode, using sodium chloride as electrolyte. The hydrogen is withdrawn from the cell, as net product, through line 11.

Chlorine produced in cell 10 is withdrawn therefrom through line 12 and introduced into an absorption tower 13, including suitable means for increasing gas-liquid contact, schematically generally indicated as 14, wherein the chlorine is countercurrently contacted with a liquid stream introduced through line 15, which is comprised of tertiary alkanol or tertiary alkanol and tertiary alkyl hypochlorite dissolved in an organic solvent, of the type hereinabove described. In particular, the liquid stream contains tertiary butyl alcohol or tertiary butyl alcohol and tertiary butyl hypochlorite dissolved in an organic solvent, which is preferably carbon tetrachloride alone, or in admixture with dichloropropane. The absorption is generally effected at a temperature in the order of from 30° F. to 200° F., and at a pressure in the order of from about 10 to about 30 psia.

Chlorine dissolved in the liquid, containing tertiary butanol, tertiary butyl hypochlorite, carbon tetrachloride and dichloropropane, is withdrawn from tower 13 through line 16 and introduced into a hypochlorite production reactor, in the form of a tower 17. Caustic cell liquor, containing sodium hydroxide and sodium chloride, withdrawn from electrolysis cell 10 through line 18 is combined with a recycle brine solution, which can contain small amounts of tertiary butyl alcohol, in line 19 and obtained as hereinafter described, and introduced through line 21 into reactor 17 to countercurrently contact the liquid, containing dissolved chlorine, introduced through line 16. A co-current agitated reactor may also be used. As a result of such countercurrent contact, tertiary butanol is converted to tertiary butyl hypochlorite. Reactor 17 is operated at the conditions hereinabove described.

A heavy organic stream, containing tertiary butyl hypochlorite dissolved in solvent, is withdrawn from reactor 17 through line 22, and a lighter aqueous saturated brine solution is withdrawn from tower 17 through line 23.

A portion of the brine solution in line 23 may be recycled to reactor 17 through line 24 including an appropriate exchanger 25.

The remaining portion of the brine solution in line 26 is then recycled to the electrolysis cell. Such brine solution may contain some minor amounts of organic contaminants, and such contaminants may be removed by a purification procedure involving chlorination of such contaminants in a purification zone, schematically generally indicated as 27. Such purification may be effected as described in U.S. Pat. No. 4,126,526, which is hereby incorporated by reference. The brine solution, with or without purification, is ultimately introduced into the electrolysis cell 10 through line 29.

A portion of the organics withdrawn from reactor 17 through line 22 may be recycled to absorption tower 13 through line 31 in order to control the concentration of the tertiary hypochlorite present in the feed introduced into the chlorohydrin production reactor and/or provide the required amount of liquid flow for absorbing chlorine in tower 13.

The remaining portion of the hypochlorite dissolved in organic solvent, in line 32, is introduced into a chlorohydrin production reaction zone, schematically generally indicated as 33. Propylene in line 34 is preferably dissolved in the organic stream in line 32 for introduction into the reactor 33. Recycle water stream in line 35 is also introduced into the chlorohydrin production reaction zone 33. The chlorohydrin production reaction zone 33 may also be provided with a catalyst in order to increase chlorohydrin production. The chlorohydrin production reaction zone 33 is operated at conditions, as hereinabove described.

The chlorohydrin production reactor 33 includes means for effecting mixing of the two liquid phases present in the reactor.

Inert gases, if present, in the reaction feed, such as propane present in a propylene stream obtained from a refinery, are vented from the reaction zone 33 through line 36. A liquid reaction effluent, which contains tertiary butanol, propylene chlorohydrin, as well as any reaction byproducts, and which further contains a light aqueous phase, is withdrawn from the reaction zone 33 through line 37 and introduced into a separator, schematically generally indicated as 38, in order to effect separation of an aqueous phase from an organic phase.

An aqueous phase, which primarily contains water, is withdrawn from the separator 38 for recycle to the reactor 33 through line 35. Make-up water may be provided to such recycle stream through line 40.

A heavier organic phase is withdrawn from separator 38 through line 39 and introduced into a saponification reactor, schematically generally indicated as 41, which is also provided with caustic cell liquor through line 42 to effect saponification of propylene chlorohydrin to propylene oxide. The saponification reactor 41 is operated at the conditions hereinabove described.

The saponification reaction effluent is flashed from reactor 41 through line 42 into a fractional distillation column, schematically generally indicated as 43, in order to separate from the effluent propylene oxide as well as any light end products; i.e., acetone. Propylene oxide is withdrawn as product through line 44, and may be further treated to effect purification thereof, as required, and known in the art.

A bottoms is withdrawn from distillation column 43 through line 45 and introduced into a separator, schematically generally indicated as 46, in order to effect separation of an aqueous phase from an organic phase. In particular, in separator 46, an aqueous brine solution, which may contain some minor amounts of tertiary butanol, is recovered through line 19 for recycle to the hypochlorite production reactor 17, as hereinabove described. Any tertiary butanol present in such stream is converted to the hypochlorite in reactor 17.

An organic stream, containing tertiary butanol dissolved in the organic solvent (in particular carbon tetrachloride-dichloropropane) is withdrawn from separator 46 through line 47 for introduction into absorption tower 13 for initial dissolution of chlorine and subsequent introduction into reactor 17 for conversion of the tertiary butanol to hypochlorite.

A slip stream of the organic phase may be withdrawn from separator 46 through line 51 and introduced into a fractional distillation column, schematically gene ally indicated as 52, in order to separate net byproduct therefrom through line 53. An overhead comprised of tertiary butanol in dichloropropane and the solvent is recovered through line 54 for ultimate recycle to the chlorine dissolution step via lines 47 and 15.

A portion of the aqueous stream 19 may be withdrawn through line 57 into the brine purification unit 27 in order to prevent buildup of propylene glycol, if such a need arises. Proportioning of aqueous solutions in lines 26 and 57 around the purification unit 27 will be determined variously according to the purity of recycle brine in line 29.

Although the invention has been particularly described with respect to a preferred integrated operation, the present invention is also applicable to the production of epoxy compounds without integration. Thus, as hereinabove indicated, alkali and/or chlorine may be provided in one or more of the operations other than by integration with an electrolytic cell for chlorine production. The conditions for producing the hypochlorite, chlorohydrin and epoxy compound are as hereinabove described with respect to the integrated process. Similarly, alkali other than sodium hydroxide; e.g., calcium hydroxide, may be employed in one or more of the steps. The above modifications and others should be apparent to those skilled in the art from the teachings herein.

The invention will be further described with respect to the following examples; however, the scope of the invention is not to be limited thereby:

EXAMPLE 1

The conversion of t-butyl alcohol in carbon tetrachloride to t-butyl hypochlorite was demonstrated in this example. In a 1.0 l capacity flask, 270 cc of an organic mixture containing 7.434% weight of t-butyl alcohol in carbon tetrachloride was charged. A 310 cc-portion of an aqueous solution containing 4.095 wt. sodium hydroxide and 27.883% wt. sodium chloride was then added. While stirring the mixture thoroughly, 30.7 g chlorine was charged at 30°-35° C. in two hours to give 96.2% yield of t-butyl hypochlorite in the organic layer. Of the active chlorine species in the organic layer, 9.7% mole was due to the dissolved free chlorine, to give a chlorine accountability of 101.5%.

EXAMPLE 2

In a 250 cc-capacity rocking autoclave, 80 cc of a t-butyl hypochlorite solution (634 mmole/l) in carbon tetrachloride was charged with 80 cc of water at 44° C. The autoclave was then pressurized with propylene to 4.10 atm. and reaction was started by rocking the autoclave. The total pressure in the autoclave was maintained at 4.0±0.1 atm. by charging propylene as consumed. After 30 minutes, the autoclave was vented and the product analyzed. The conversion of t-butyl hypochlorite was 99.96%. The chlorine accountability was 101.5% mole. The yield structure of propylene product was as follows: propylene chlorohydrin 95.3%; acetone 1.3; propionaldehyde 0.8; propylene oxide 0.1; dichloropropane 2.4; t-butyl chloroisopropyl ether 0.1 and bischloroisopropyl ether 0.1% mole of the propylene reacted.

EXAMPLE 3

The chlorohydrination run in Example 2 was repeated with 75 cc of an 845 mmole/l solution of t-butyl hypochlorite and 75 cc of water at 50° C. in 30 minutes. The hypochlorite conversion was better than 99.94%. The chlorine accountability was 104.0% mole. The yield structure of propylene products was 94.9% propylene chlorohydrin, 1.2% acetone, 0.7% propionaldehyde, 0.1% chloroacetone, 2.6% dichloropropane, 0.1% t-butyl chloroisopropyl ether, 0.2% bischloroisopropyl ether and 0.2% mole propylene oxide.

EXAMPLE 4

The above test run was repeated with an 1268 mmole/l solution of t-butyl hypochlorite in carbon tetrachloride to give 99.90% conversion of the hypochlorite. The propylene product yields were propylene chlorohydrin 90.5%, acetone 1.9%, propionaldehyde 0.9%, propylene oxide 0.3%, dichloropropane 5.4%, t-butyl chloroisopropyl ether 0.4% and bischloroisopropyl ether 0.6% mole.

EXAMPLE 5

A dichloropropane solution containing 0.2 wt% water, 5.0 wt. t-butyl alcohol and 6.0 wt% propylene chlorohydrin was used as an organic feed. The chlorohydrin content corresponded to 0.708 mol/L. At a rate of 16.0 cc/min, the feed was mixed with 12.3 cc/min of a brine containing 3.59 wt% sodium hydroxide (1.006 mol/L). The mixture was saponified for about one minute at 90°-95° C., 2 atm., and then was charged into the midpoint of a distillation column. The reboiler temperature was 80±2° C. and the overhead temperature 35±2° C., at a reflux ratio of 30/1. The overhead was collected at approximately 1.1 cc/min and the bottoms withdrawn at about 27 cc/min. During a 40-minute period, beginning after 130 minutes into the run, the following data were obtained:

| | |
|---|---|
| Caustic/chlorohydrin charge ratio (molar) | = 1.087/1.000 |
| Conversion of the chlorohydrin | = 99.62% |
| Net caustic reacted/chlorohydrin reacted (molar) | = 0.897/1.000 |
| Total propylene oxide generated | = 422.11 mmol |
| Selectivity to propylene oxide | = 99.03 mol % |
| Propylene glycol in the bottoms | = below the limit of detection at 0.001 wt % |

EXAMPLE 6

The caustic stream, identical to Example 1, was introduced into the same saponifier/distillation column at 21.0 cc/min. A second organic feed containing 0.87% water, 14.80% t-butyl alcohol and 17.15% propylene chlorohydrin (1.933 mol/L) in dichloropropane was charged at a rate of 10.8 cc/min. The column reflux ratio was set at 10/1. During a 20-minute period, beginning after 160 minutes into the run, the following data were obtained:

| | |
|---|---|
| Caustic/chlorohydrin charge ratio (molar) | = 1.026/1.000 |
| Conversion of the chlorohydrin | = 99.38% |
| Net caustic reacted/chlorohydrin reacted (molar) | = 1.035/1.000 |
| Total propylene oxide generated | = 395.13 mmol |
| Selectivity to propylene oxide | = 96.78 mol % |
| Propylene glycol in the bottoms | = below the limit of detection at 0.001 wt % |

EXAMPLE 7

The organic feed, identical to Example 6, was charged into the saponification reactor/distillation column at a rate of 15.6 cc/min. A brine containing 8.13 wt%, or 2.310 mol/L of caustic, was charged at a rate of 13.7 cc/min. After a continuous run of 170 minutes, the following data were obtained at a reflux ratio of 10/1:

| | |
|---|---|
| Caustic/chlorohydrin charge ratio (molar) | = 1.051/1.000 |
| Conversion of the chlorohydrin | = 99.25% |
| Net caustic reacted/chlorohydrin reacted (molar) | = 1.007/1.000 |
| Total propylene oxide generated | = 5071.24 mmol |
| Selectivity to propylene Oxide | = 98.44 mol % |
| Propylene glycol in the bottoms | = below the limit of detection at 0.001 wt % |

Numerous modifications and variations of the present invention are possible in light of the above teachings and, therefore, within the scope of the appended claims, the invention may be practised otherwise than as particularly described.

We claim:

1. A process for converting an olefinically unsaturated compound to the corresponding epoxy compound, comprising:
contacting a tertiary alkanol in an inert organic solvent, chlorine and aqueous alkali to produce tertiary alkyl hypochlorite, at a temperature of from 5° to 220° F.; separating an organic phase of tertiary alkyl hypochlorite in the inert organic solvent; contacting tertiary alkyl hypochlorite in the inert organic solvent, water and an olefinically unsaturated compound to produce the corresponding chlorohydrin and a tertiary alkanol, at a temperature of from 32° F. to 160° F. said water having a salt dissolved therein to enhance extraction of the tertiary alkanol and chlorohydrin into the inert organic solvent; separating an organic phase of chlorohydrin and tertiary alkanol in the inert organic solvent; contacting cholorohydrin and tertiary alkanol in the inert organic solvent and aqueous alkali to convert the chlorohydrin to the corresponding epoxy compound; recovering said epoxy compound; separating an organic phase of the tertiary alkanol in the inert organic solvent; and passing tertiary alkanol in the inert organic solvent to the contacting with chlorine and aqueous alkali.

2. The process of claim 1 wherein the chlorine and tertiary alkanol are dissolved in the inert organic solvent for the production of tertiary alkyl hypochlorite prior to contacting with aqueous alkali.

3. The process of claim 2 wherein the inert organic solvent is comprised of at least one chlorinated hydrocarbon.

4. The process of claim 3 wherein the tertiary alkanol is tertiary butanol.

5. The process of claim 1 wherein a water phase is recovered from the chlorohydrin production and recycled to the chlorohydrin production.

6. The process of claim 1 wherein a water phase is recovered from the epoxy compound production, said water phase including tertiary alkanol and being passed to the contacting with chlorine and alkali to convert the tertiary alkanol to tertiary alkyl hypochlorite.

7. The process of claim 1 wherein the olefinically unsaturated compound is a compound selected from the group consisting of compounds with the following structural formula:

$$R_1-CH=CH-R_2$$

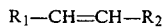

wherein $R_1$ and $R_2$ are each separately selected from the group consisting of hydrogen; alkyl; halo-, naphthyl and phenyl substituted alkyl; phenyl; halo- and alkyl substituted phenyl; naphthyl; halo- and alkyl substituted naphthyl; alkenyl and halo-substituted alkenyl; and $R_1$ and $R_2$ can be linked together to provide a cycloalkene having from 5–10 carbon atoms.

8. The process of claim 10 wherein the olefinically unsaturated compound is propylene.

9. The process of claim 10 wherein the olefinically unsaturated compound is allyl chloride.

10. A process for converting an olefinically unsaturated compound to the corresponding epoxy compound, comprising:
contacting a tertiary alkanol in an inert organic solvent, chlorine and aqueous electrolyte containing sodium chloride and sodium hydroxide obtained from an electrolytic cell for producing chlorine to produce tertiary alkyl hypochlorite and an aqueous brine; separating an organic phase of tertiary alkyl hypochlorite in the inert organic solvent from aqueous brine for recycle of aqueous brine to the electrolytic cell; contacting tertiary alkyl hypochlorite in the inert organic solvent, water and an olefinically unsaturated compound to produce the corresponding chlorohydrin and tertiary alkanol, said water having a salt dissolved therein to enhance extraction of the tertiary alkanol and chlorohydrin into the inert organic solvent; separating an organic phase of chlorohydrin and tertiary alkanol in the inert organic solvent; contacting chlorohydrin and tertiary alkanol in the inert organic solvent and aqueous electrolyte containing sodium chloride and sodium hydroxide from the electrolytic cell to convert the chlorohydrin to the corresponding epoxy compound and produce aqueous brine; recovering the epoxy compound; separating an aqueous brine phase from an organic phase of tertiary alkanol in the inert organic solvent; passing tertiary alkanol in the inert organic solvent to the contacting with chlorine and aqueous electrolyte; employing aqueous brine generated in producing epoxy compound in the contacting of tertiary alkanol with chlorine and electrolyte prior to recycle to the cell to convert any tertiary alkanol present therein to tertiary alkyl hypochlorite; recovering from the chlorohydrin production a water phase; and recycling recovered water phase to the chlorohydrin production.

11. The process of claim 13 wherein the chlorine and tertiary alkanol are dissolved in the inert organic solvent for the production of tertiary alkyl hypochlorite prior to contacting with the aqueous electrolyte.

12. The process of claim 11 wherein the inert organic solvent is comprised of at least one chlorinated hydrocarbon.

13. The process of claim 11 wherein the hypochlorite production is effected at a temperature of from 5° F. to 220° F.

14. The process of claim 13 wherein the chlorohydrin production is effected at a temperature of from 32° F. to 160° F.

15. The process of claim 14 wherein the olefinically unsaturated compound is a compound selected from the group consisting of compounds with the following structural formula:

$$R_1-CH=CH-R_2$$

wherein $R_1$ and $R_2$ are each separately selected from the group consisting of hydrogen; alkyl; halo-, naphthyl and phenyl substituted alkyl; phenyl; halo- and alkyl substituted phenyl; naphthyl; halo- and alkyl substituted naphthyl; alkenyl and halo-substituted alkenyl; and $R_1$ and $R_2$ can be linked together to provide a cycloalkene having from 5–10 carbon atoms.

16. The process of claim 15 wherein the tertiary alkanol is tertiary butanol.

17. The process of claim 16 wherein the olefinically unsaturated compound is propylene.

18. The process of claim 16 wherein the olefinically unsaturated compound is allyl chloride.

* * * * *